United States Patent [19]
Stolarczyk et al.

[11] Patent Number: 5,474,261
[45] Date of Patent: Dec. 12, 1995

[54] ICE DETECTION APPARATUS FOR TRANSPORTATION SAFETY

[75] Inventors: Larry G. Stolarczyk; Gerald L. Stolarczyk, both of Raton, N.M.

[73] Assignee: Raton Technology Research, Inc., Raton, N.M.

[21] Appl. No.: 123,562

[22] Filed: Sep. 20, 1993

[51] Int. Cl.⁶ .................................................. B64D 15/20
[52] U.S. Cl. ..................................... 244/134 F; 340/582
[58] Field of Search ........................... 244/134 R, 134 F, 244/134 D; 340/582; 324/332

[56] References Cited

U.S. PATENT DOCUMENTS

| | | | |
|---|---|---|---|
| 2,419,454 | 4/1947 | LeClair | 340/582 |
| 3,240,054 | 3/1966 | Roth | 340/582 |
| 3,781,566 | 12/1973 | Meuller | 340/582 |
| 4,568,922 | 2/1986 | Schwippert et al. | 340/582 |
| 4,628,736 | 12/1986 | Kirby et al. | 340/582 |
| 4,891,796 | 1/1990 | Sekine | 340/582 |
| 5,072,172 | 12/1991 | Stolarczyk | 324/332 |

OTHER PUBLICATIONS

R. N. Grubb, P. L. Orswell, J. H. Taylor, "Borehole measurements of conductivity and dielectric constant in the 300 KHz to 25 MHz frequency range," Radio Science, vol. 11, No. 4, pp. 275–283, Apr. 1976 (Published by the American Geophysical Union, Washington, D.C.).

*Primary Examiner*—Galen L. Barefoot
*Attorney, Agent, or Firm*—Thomas E. Schatzel

[57] ABSTRACT

An embodiment of the present invention is an ice detection system that comprises a network of thin, flexible microstrip antennas distributed on an aircraft wing at critical points and multiplexed into a microcomputer. Each sensor antenna and associated electronics measures the unique electrical properties of compounds that accumulate on the wing surface over the sensor. The electronics include provisions for sensor fusion wherein thermocouple and acoustic data values are measured. A microcomputer processes the information and can discern the presence of ice, water frost, ethylene-glycol or slush. A program executing in the microcomputer can recognize each compound's characteristic signal and can calculate the compounds' thicknesses and can predict how quickly the substance is progressing toward icing conditions. A flight deck readout enables a pilot or ground crew to be informed as to whether deicing procedures are necessary and/or how soon deicing may be necessary.

10 Claims, 5 Drawing Sheets

ICE DETECTION APPARATUS FOR TRANSPORTATION SAFETY

RELATED APPLICATIONS

This application is related to copending application Ser. No. 07/982,829, filed Nov. 30, 1992, by the present inventors, and is hereby incorporated by reference and made a part of this application.

BACKGROUND OF THE INVENTION

1. Field of the Invention

The invention relates generally to transportation safety equipment and instruments and specifically to devices capable of detecting and measuring liquid water and/or ice accumulation layer, such as can occur on the surfaces of airplane wings and space craft prior to launch.

2. Description of the Prior Art

Ice build-up on low temperature fuel tanks, airfoil surfaces and highways can unexpectedly occur and create hazardous conditions for transportation.

Any amount of ice or slush is considered a contaminant on a wing and presents a potential hazard, therefore the regulations of the Federal Aviation Administration outlined the "clean wing" concept: before an aircraft takes off, there can be no ice present on the airfoil (the wing and upright tail assembly). The "clean wing" concept will have been achieved when (under icing conditions) an aircraft has been properly deiced and, if freezing precipitation is occurring, anti-iced with a fluid having an adequate holdover time interval between the start of anti-icing and the start of takeoff.

Despite this precise regulation, incidents regularly occur that indicate that pilots may not always be able to readily detect the ice buildup and may take off with ice still adhering to the surface of the wing or tail.

While various methods have been tested, currently no product has been approved by the FAA that can measure whether there is ice on the airfoil, discriminate that from other fluids that might be on the wing such as deicer or slush or frost or water, and report to the pilot the relative safety of the aircraft. Various techniques including ultrasonic, lasers, fluorescent dyes and vibrating probes have been tried unsuccessfully. The natural water layer on top of the ice has been a major obstacle in finding a solution. Currently ice detection is done in a low-tech, manual fashion: visually by the pilot and/or one or more members of the ground crew. Under normal winter procedures the top of the wing is inspected for ice when the ambient temp is below 32° F. As the temperature and other climatic conditions change, varying degrees of inspection are required. While the visual inspection is the main method of detection, at least a dozen interrelated variables actually contribute to the detection of ice on the airfoil: ambient temperature, aircraft surface temperature, relative humidity, solar radiation, wind velocity and direction, presence of deicing fluid, type of deicing fluid and its strength, the deicing procedure used, proximity to other aircraft, equipment and buildings, and the aircraft component inclination. All of these combine in varying degrees to make the situation for ice to form.

Ice build-up, such as on the low temperature fuel tanks of space shuttles, is also a safety concern. After filling the insulated fuel tanks on a booster rocket, the countdown time period is allowed to continue unless any ice build-up is one-quarter inch thick or more. Presently, ice depth measurements are done manually by workers who scratch away at an ice layer and measure the ice layer thickness.

Commercial airline disasters in Washington D.C., Denver, Colo., Newfoundland, and recently in Europe, have been suspected to have been caused by ice and snow build-up on the wings of the aircraft. In a preventative attempt to alleviate the potential dangers of ice and snow, air maintenance crews universally spray air foil surfaces with a deicing and anti-icing liquid, e.g., ethylene-glycol, at times not caring whether any ice is actually present. In bad weather operating conditions, takeoffs of planes are often delayed because the weather reduces the number of planes that can takeoff and land, which only exacerbates the icing problem because more time is available for the ice to build-up on wings to dangerous thicknesses. This reduces the hold time of the aircraft before takeoff. Hot ethylene-glycol fluid may be sprayed on airfoil surfaces for deicing purposes. Anti-icing ethylene-glycol fluids are sprayed on airfoil surfaces to create a layer for clearing off a wing during takeoff. As snow or rain continues to accumulate, the freezing-point temperature of the anti-freeze mixture increases. During a taxi and hold period, the effectiveness of the anti-icing fluid is compromised. A pilot's vision of his aircraft's surfaces is usually very limited. Pilots waiting to takeoff need a reliable sensor technology that can determine if critical airfoil surfaces have been compromised. Any ice thickness, snow thickness, and slush-ethylene glycol mixture thickness are all important data a pilot would want to have reported. The freezing point of the anti-icing layer must be known.

General aviation operating in icing conditions typically employ deicing technology to remove dangerous ice formations from air foil surfaces. Ice has a tendency to form on the leading edges and other protruding surfaces of an aircraft's superstructure during flight. Through the years, deicing technology has been developed that includes pneumatic bladders, heating elements, and ultrasonic transducers. Such technology requires in-flight fuel during operation.

Many prior art technologies have been investigated and dismissed as being unreliable in their ability to measure ice build-up under adverse weather conditions. One of the technical problems relates to the discrimination of ice, snow, and water conditions on the surface. Another relates to the measurement of the freezing-point of an anti-freeze mixture. Measurement of the overlying material thickness is another problem. The measurement depends on the electrical parameters of the particular layer and a method of measuring the electrical parameters of the layer is needed. The same technology is needed to determine the freezing-point of an anti-freeze mixture. Sensor wear is yet another problem. For example, sensors that protrude may unreliably determine ice conditions on airfoil surfaces. A flush sensor that can be conformably mounted is needed. Such a sensor must also be compatible with the thermodynamic properties of surrounding surfaces that are to be monitored by the sensor.

Theoretical and experimental studies of microstrip antennas have shown that an antenna's terminal admittance can be made to be dependent on the depth and dielectric constant and electrical conductivity of an ice, snow, water, water-ethylene glycol or coal layer overlying the antenna. For background art, see U.S. Pat. No. 5,072,172, issued Dec. 10, 1991, and especially the discussion relating to FIG. 10, an airplane wing cross-section. Microstrip antennas are typically constructed by forming conductive layers on a substrate with a relative dielectric constant ($\epsilon_r$) greater than 2.2. The requisite physical size of an antenna will decrease with increases in the dielectric constant. Typical values of relative dielectric constant vary from 2.2 for DUROID™, to approximately 9.8 for TMM-10™ substrate material, which has a lower temperature coefficient. Higher dielectric constant substrates are also technically possible. A microstrip patch may be circular, rectangular or spiral in form. The spiral type may be considered to be a narrow rectangular line with radiation occurring along the edges of a microstrip line. The spiral form may be more sensitive to ice thickness.

Today, there is no working device that is approved for airline use that can measure the presence of ice, slush, snow or water on an aircraft wing, and tell the pilot whether it is safe to take off.

Ice buildup on the massive space shuttle's external tank has always been a safety concern prior to launch into orbit. Ice sloughing-off from the low temperature fuel tanks during launch can damage windows and heat shield tiles on the space shuttle, potentially causing a catastrophic emergency, either at liftoff or on reentry. Therefore, launch criteria requires that there must be no ice formations in an area that could damage windows, and there must be no ice acreage with thickness greater than one-sixteenth inch that could break loose and strike the space shuttle's heat shield tiles and thereby compromise its ability to safely return to earth.

Despite the extraordinary technology developments in many space projects, sensors that can detect ice on the fuel tanks of the space shuttle have not been developed and this problem still persists. Presently, an "ice team" manually scratches the airfoil surfaces to detect ice and measure its thickness. On the large upright external tank, the number of manual measurements possible is limited by practical constraints.

SUMMARY OF THE PRESENT INVENTION

It is therefore an object of the present invention to provide a monitoring system for measuring the presence and thickness of ice on a surface exposed to the weather.

It is a further object of the present invention to provide a means for measuring the freezing point of a water-glycol mixture on an airfoil surface.

It is a further object of the present invention to provide an automatic means for warning pilots in the cockpit or via the control tower of the hazards from icing conditions existing on an airplane's airfoils.

It is a further object of the present invention to provide an automatic means for warning mission control personnel of the hazards from ice accumulations existing on a spacecraft liquid oxygen tank.

Briefly, an ice detection system embodiment of the present invention comprises a network of thin, flexible microstrip antennas distributed on an aircraft wing at critical points and multiplexed into a microcomputer. Each sensor antenna and associated electronics measures the unique electrical properties of the compounds that accumulate on the wing surface over the sensor. The electronics include provisions for sensor fusion wherein thermocouple and acoustic data values are measured. A microcomputer in the electronics processes the information and discerns the presence of ice, water frost, ethylene-glycol or slush. A program executing in the microcomputer can recognize each compound's characteristic signal and can calculate the compounds' thicknesses and can predict how quickly the substance is progressing toward icing conditions. A flight deck readout enables a pilot or ground crew to be informed as to whether deicing procedures are necessary and/or how soon deicing may be necessary.

An advantage of the present invention is that a system is provided that enables a pilot and ground crew to know the condition of an airfoil across multiple dimensions. It further can inform users what substances are on the airfoil, whether those substances comprise one layer of multiple layers, the thicknesses of each layer, and the amount of time allotted by FAA regulations before that aircraft has to be again checked for icing conditions A further advantage of the present invention is that a system is provided that can detect and measure ice and water accumulation layers on a surface exposed to the weather.

Another advantage of the present invention is that a system is provided that can indicate exactly when and where de-icing and anti-icing procedures are required for an airplane's wings.

These and other objects and advantages of the present invention will no doubt become obvious to those of ordinary skill in the art after having read the following detailed description of the preferred embodiment that is illustrated in the various drawing figures.

IN THE DRAWINGS

DETAILED DESCRIPTION OF THE PREFERRED EMBODIMENTS

Figure 1:
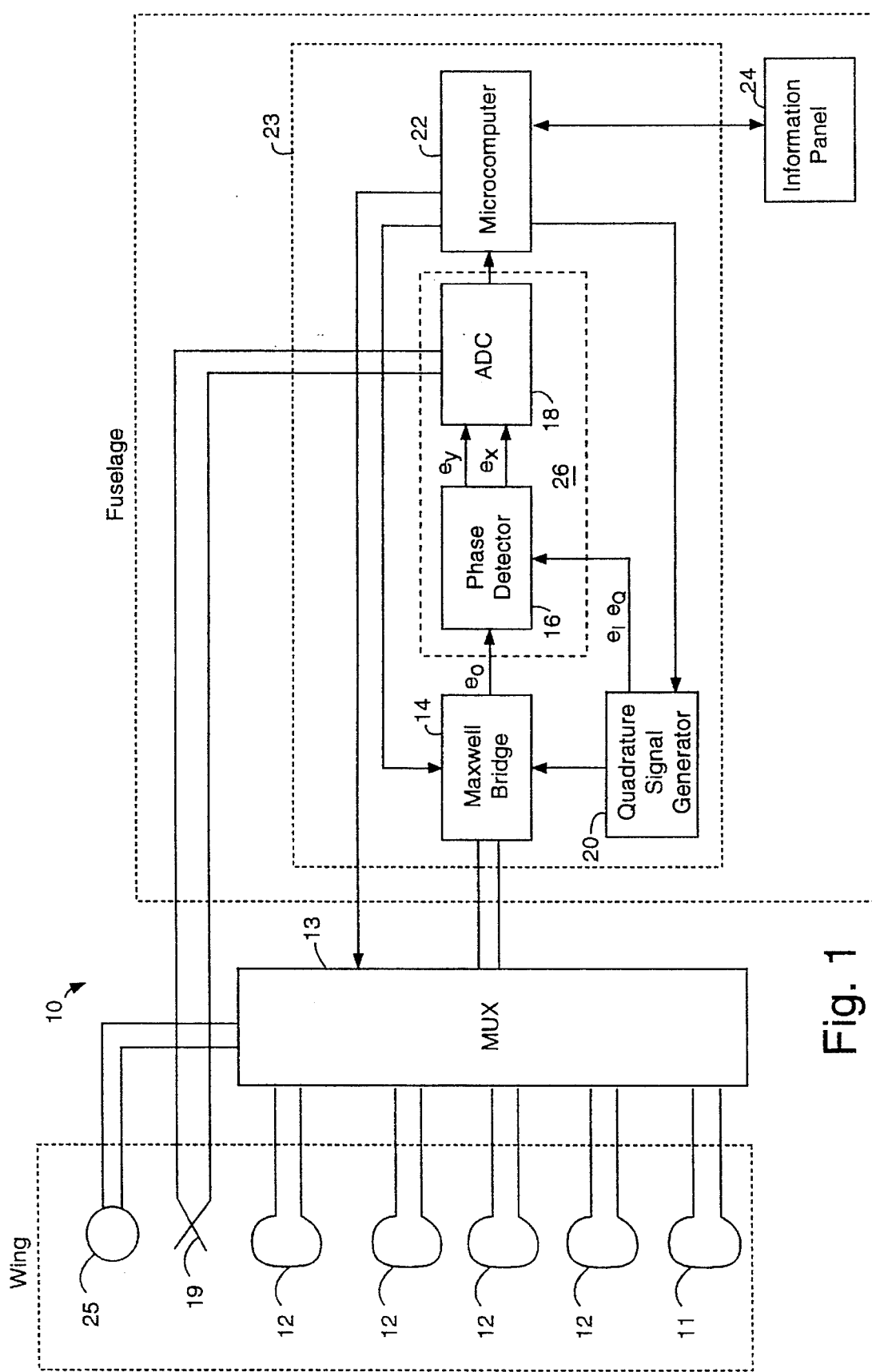
FIG. 1 is a block diagram of a system embodiment of the present invention for detecting and measuring ice and water accumulations.

FIG. 1 illustrates a transportation safety icing detection system embodiment of the present invention, referred to herein by the general reference numeral 10. System 10 comprises a calibration antenna 11, a plurality of patch antennas 12, a multiplexer (MUX) 13, a Maxwell bridge 14, a phase detector 16, an analog-to-digital converter (ADC) 18, a thermocouple 19, a quadrature signal generator (QSG) 20, a microcomputer 22, a fuselage instrument housing 23 and a pilot information display 24.

An acoustic sensor 25 is connected to MUX 13. Sensor 25 may, for example, comprise a piezoelectric device that is affected in its natural resonant frequency by viscous liquids and or solids that come in contact with it or attach to it. Sensor 25 is preferably mounted in places similar to those for antennas 12 and can provide additional information about ice droplets or ice layers that become frozen to it. Such additional data can assist a program running in microcomputer 22 to characterize the accumulations of material, e.g., on an airfoil.

Antennas 11 and 12 are circular patch antennas operated at microwave frequencies and having an offset coaxial feedspoint which presents an admittance input term $Y_{in}$. Antenna 11 provides a standard set of electrical characteristics that simulate those that are characteristic of antennas 12 during an ice condition. To simulate such an ice condition, antenna 11 may, for example, be permanently attached to a block of material that mimics the effects of ice on the resonant frequency and input admittance of antenna 11 and serves as a reference for measurements from antennas 12.

The MUX 13 may either time-division or frequency-division multiplex each antenna 11 and 12 into the Maxwell bridge 14 for icing measurements. Microcomputer 22 selects which multiplexer input will be active at any one time. Circuits that can do such multiplexing are conventional and further detail is unnecessary here.

Thermocouple 19 provides for a measurement of the temperature ambient to antennas 12. Temperature measurements taken over a period of time can be assembled, e.g., in a database in microcomputer 22, for interpretation of current icing trends. For example, pilots of aircraft need to know whether the airfoil surfaces of the wings of their aircraft are advancing toward a freezing temperature or away from such freezing temperature. Armed with such information, a pilot can anticipate whether a deicing treatment will be required. The actual temperature point that liquids on the wing will freeze is affected by the composition of the materials within the liquid. A pure water composition will freeze at a higher temperature than will one that contains significant amounts of anti-freeze. The acoustic sensor 25 measures the physical properties of the overlaying layer (density and viscosity). This data can be used to determine adhesion. Therefore, system 10 preferably further determines with a computer program the freezing point of the mixture actually present on the wing by various measurements described herein.

Microcomputer 22 alternatively provides a calibration signal to bridge 14 and a frequency control signal to generator 20. Bridge 14 receives a variable frequency drive signal from QSG 20 to determine the resonant frequencies of antennas 11 and 12.

System 10 measures a resonant frequency ($f_r$) and an input admittance value for each microstrip antenna 12. The input admittance (Y) is, $$Y=G+iB, \quad (1)$$

where,

G=input conductance of the antenna in Siemens and

B=input susceptance.

At a resonant frequency ($f_r$) for each antenna 11 and 12, the input susceptance (B) will equal zero. If MUX 13 is a frequency-division type, the resonant frequencies of each antenna 11 and 12 will be different so that they may be frequency discriminated.

Sensor admittance measurements are made with a Maxwell bridge configuration, embodied in bridge 14. A bridge output signal ($e_o$) is applied to a phase sensitive detector (PSD) network 26, comprised of phase detector 16 and ADC 18, and is measured by the combination of ADC 18 and microcomputer 22. A control program included in microcomputer 22 computes the admittance, using a pair of measured values for signals $e_x$ and $e_y$ that are acquired via ADC 18. Microcomputer 22 also controls the operating frequency of QSG 20 to determine a resonant frequency ($f_r$) for antenna 12.

This is done by incrementing the output frequency ($f_o$) of QSG 20 until the measured input susceptance (B) approaches zero.

Such bridge measurements necessitate that a calibration means be included within antenna 12. For example, antenna 11 can provide such calibration. Alternatively, the antenna connections can be such that an open, a short and a fifty ohm resistance are switched around to gauge the calibration.

Embodiments of the present invention measure both the composition of the layers on an airfoil and their thickness. In the case of water or ethylene-glycol, they also estimate the time before those layers become ice. Thermocouple 19 assists in a determination of whether the outside weather conditions are advancing toward icing, e.g., below freezing temperatures, or away.

Figure 2:
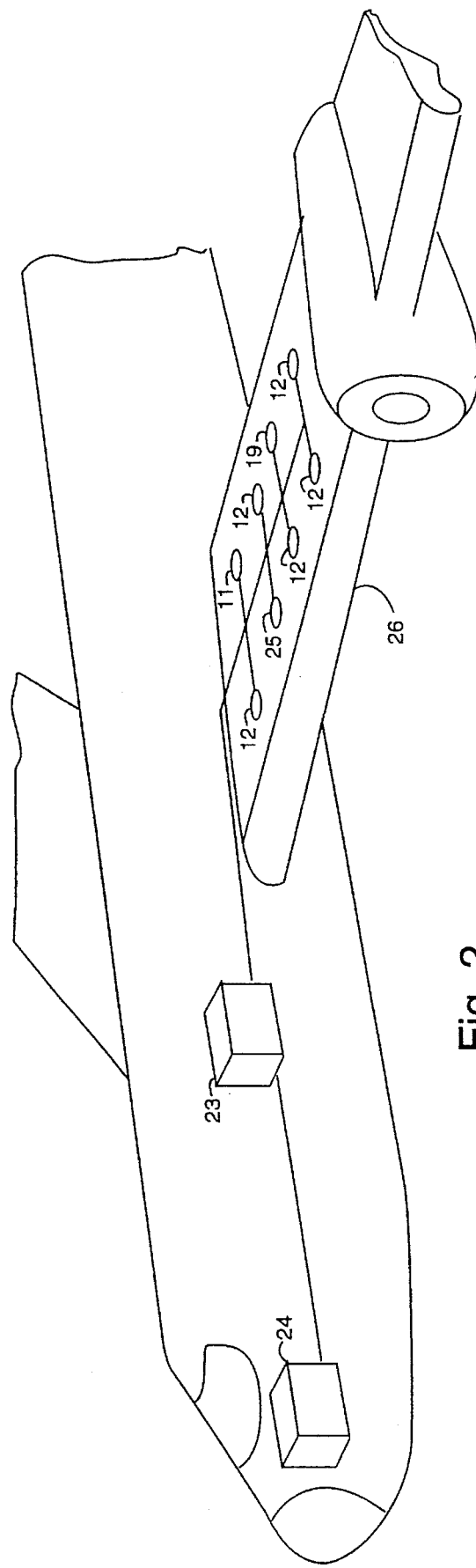
FIG. 2 is a perspective view of a part of an airplane wing and fuselage to which the system of FIG. 1 may be mounted.

FIG. 2 illustrates an airfoil 26 with antennas 11 and 12 and thermocouple 19 mounted to it. To make the measurements that detect ice or other compounds that might be on the airfoil, each antenna 12 sends out a small electric field at microwave frequencies and measures the electrical properties of the overlaying layer and the various substances of that layer, such as water, ice, slush and de-icing fluids, which all have detectable unique electrical properties.

In the absence of a layer of ice, water, etc., a primary electric field exists. When a layer forms, this causes a secondary electric field. System 10 can measure the presence of the secondary electric field, because it causes both the resonant frequency and impedance of the antenna to change in different degrees in the presence of ice, water, ethylene-glycol and slush. The system 10 further measures the strength of the electric field.

A combination of the resonant frequency and impedance measurements enable a calculation of the thickness of the layer overlaying the antennas 12, from empirical data. An identification can be made of substances on the surface of the airfoil 26, its thickness, whether it is a single layer of substance or multiple layers, and, with the microcomputer 22 and the associated electronics, to know whether and how quickly the airfoil 26 surface is progressing toward icing conditions. Such interpretations ! can be displayed on information panel 24 with the aid of color-coded CRT screen graphics. This enables a pilot or ground crew to determine whether deicing procedures are necessary, how long before deicing is necessary, and the potential time before icing conditions will exist on the airfoil 26 and deicing will be necessary, e.g., "holdover" time.

Figure 3:
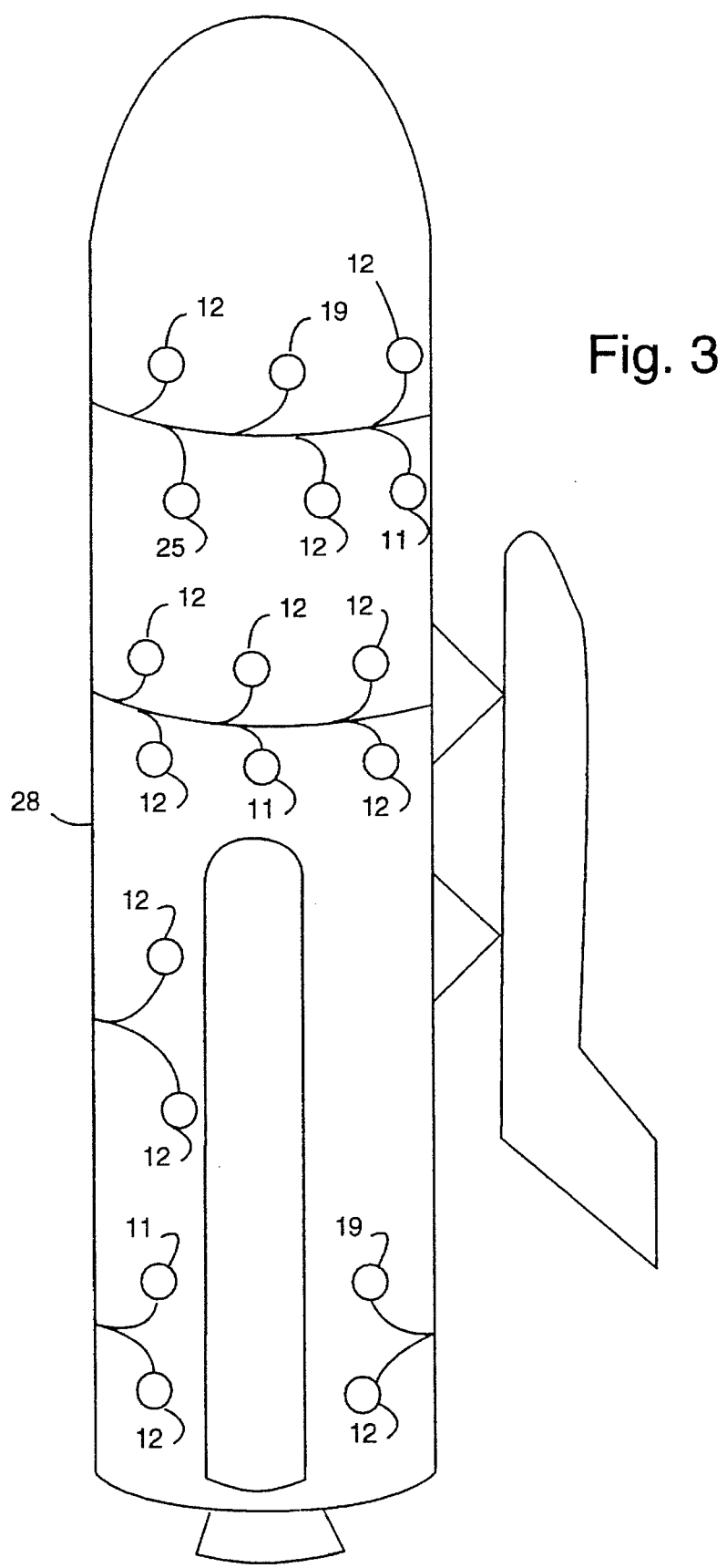
FIG. 3 is a side view of a space shuttle to which the system of FIG. 1 may be mounted.

The antennas 12 are thin, about one-tenth inch thick, and can be mounted at various places on the wing and tail assembly of an aircraft, or at strategic points on a fuel tank 28 of the space shuttle, FIG. 3. The system is preferably flexible to conform to the shape of the wing/tank on which it is fixed. The space shuttle is subject to ice formation on its large liquid fuel tank that can break-off after lift-off and during orbit insertion. The loose chunks of ice can damage the windows and heat shield tiles of the space shuttle and thereby cause a mission failure. Therefore, launches are prevented whenever excessive amounts of ice are formed on the tank before lift-off. System 10 can determine if the amounts of ice exceed predetermined maximums and can inform mission control personal via a display, such as information panel 24.

Airfoil 26 derives the major part of its lift from only a relatively small area of the wing, e.g., thirty percent outward and twenty percent back from the leading edge. As many antennas 12 as are necessary for proper detection of airfoil ice corruption form an array.

Alternatively, readings from the antennas 11 and 12 and thermocouple may be radio transmitted to housing 23, located in the fuselage of the aircraft, to avoid wiring. Conventional radio receivers and transmitters may be included in system 10 to establish such links. Otherwise, coaxial cables with multiplexed signals from each sensor can be used to interconnect with the housing 23. These interconnections may require the use of matching transformers, according to conventional practice. The flight deck or ground station readout 24 is preferably capable of reading measurements derived from each antenna 11 and 12 individually, or having antennas 12 grouped into a single reading, e.g., to indicate the presence and thickness of ice.

The microcomputer 22 and associated electronics compute what substances are present on the airfoil 26 and estimate the respective thicknesses of the substances. It analyzes the data to simplify the reporting to the flight deck or a ground station in a simplified display indicating a clean wing versus ice. The microcomputer 22 determines the composition of the compound on the airfoil 26, calculating whether it is water, ice., slush or deicing solution, or a combination of one or more of those. A digital time display may be included to indicate a time-to-ice, as calculated by the microcomputer 22. This informs the pilot if ice is forming or nearly forming, and how much time remains before it will become necessary to have the airfoil 26 deiced or have the deicing repeated.

The display configuration may be user-specific. Thus, if a user wishes to be able to have each antenna 11 and 12 or group of antennas 12 read individually, that type of readout configuration can easily be designed.

As a safety precaution, system 10 is preferably self-diagnosing. Programs included in the microcomputer 22 preferably test the system 10 to validate that it is working properly and will inform the user if the system 10 is in need of attention. Thus, preventing a user from relying on a system whose readings are not completely accurate.

After a measurement of the frequency and conductance at resonance has been completed, data including an identification number for the particular system 10 is used to frequency modulate the output signal of QSG 20. Patch antennas 12 may be used to transmit the data to a remote monitoring receiver, e.g., whenever icing is detected.

Figure 4:
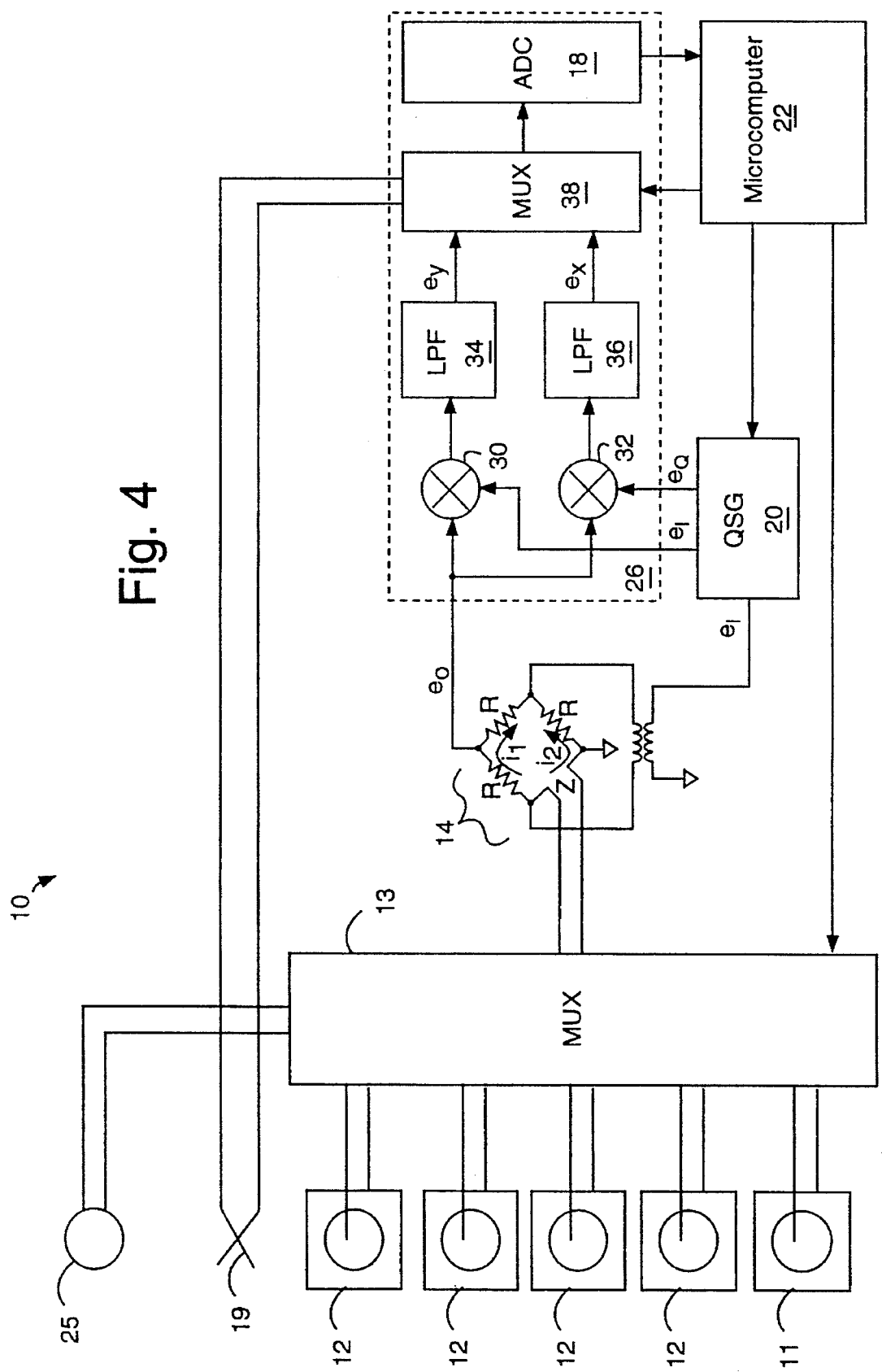
FIG. 4 is a schematic diagram that provides additional detail of selected elements of the system of FIG. 1.

FIG. 4 illustrates bridge 14 and PSD 26 in greater detail. The input impedance of microstrip antennas 12 are measured through MUX 13 with Maxwell bridge 14, PSD 26 and QSD 20. The mathematical functions of each are empirically determined. Equations for bridge 14 are derived from the network current loop equations as, $$i_1 = \frac{e}{R+R},  \qquad (2)$$

$$i_2 = \frac{e}{R+Z},  \qquad (3)$$

where
  Z is the input impedance of the antenna,
  R is the bridge resistance value in ohms, and,
  $e = E \sin(2\pi f_r t + \theta_1)$ is the bridge source voltage,
  where
    E is the peak value of the source voltage, $f_r$ is the operating frequency in Hertz of QSD 20, and
    $\theta_1$ is the phase of the QSD signal.

The bridge network output voltage ($e_o$) is, $$e_o = (i_2 - i_1)R. \qquad (4)$$

Substituting equations (2) and (3) into equation (4) results in the bridge voltage ratio $\Gamma$ being defined in terms of the bridge impedances, $$\Gamma = \frac{e_o}{e} = \frac{R}{R+Z} - \frac{R}{R+R}. \qquad (5)$$

The ratio is a complex number that can be represented by, $$\Gamma = |\Gamma| e^{-i\theta_M}, \qquad (6)$$

where
  $|\Gamma|$ is the magnitude-of the ratio, and
  $\theta_M$ is the measured phase shift.

The antenna input impedance can be computed from, $$Z = \left[ \frac{\frac{1}{2} - \Gamma}{\frac{1}{2} + \Gamma} \right] R. \qquad (7)$$

To maximize the change in bridge voltage ratio $\Gamma$ with a change in Z, it can be shown that the bridge R value should be set equal to real value of Z at resonant frequency of a particular antenna 12.

The measurement of the bridge voltage ratio ($\Gamma = e_o/e$) requires that the magnitude and phase of the bridge source voltage (e) be known, thus calibration is needed. By shorting the two terminals of any antenna 12, an inspection of the bridge network shows that the measured output voltage ($e_o$) is, $$e_o = \tfrac{1}{2} e. \qquad (8)$$

By opening the two terminals of the antenna 12, the bridge network output voltage becomes, $$e_o = -\tfrac{1}{2} e. \qquad (9)$$

The open circuit condition produces an output voltage that is 180 degrees out of phase with the short circuit condition. In either case, the magnitude of the calibrated bridge output voltage will be one-half of QSD 20 source voltage (e). The magnitude of the quadrature signal is, $$E = 2 e_o. \qquad (10)$$

Phase calibration of system 10 can be established from the open and short-circuit phase data (180°). However, this data is not needed if a synchronous detector is used for the phase sensitive detector network.

The bridge output signal may be represented by, $$e_o = \tfrac{1}{2} |\Gamma| E \ \text{SIN} \ (2\pi f_r t + q_1 + \theta_M). \qquad (11)$$

FIG. 4 shows that PSD 26 comprises a pair of mixers 30 and 32 which respectively mix an in-phase injection signal $e_I$ and a quadrature-phase injection signal $e_Q$ with output voltage $e_o$ from bridge 14, expressed as, $$e_o \times e_I, \qquad (12)$$

$$e_o \times e_Q. \qquad (13)$$

A pair of lowpass filters 34 and 36 respectively produce voltages $e_x$ and $e_y$. A multiplexer 38 is controlled by the microcomputer 22 to select an input signal for ADC 18. QSD 20 outputs sinusoid signals that are represented by:

$$e_I = E \ \text{SIN} \ (\omega t + \theta_1), \qquad (14)$$

and $$e_Q = E \ \text{SIN} \ (\omega t + \theta_1 + 90°). \qquad (15)$$

Lowpass filtering of the mixer output signals results in an elimination of all frequency dependent terms, except the DC terms, as in:

$$e_x = \tfrac{1}{2} |\Gamma| E^2 \ \text{SIN} \ (\theta_M + \theta_1 - \theta_1), \qquad (16)$$

and $$e_y = \tfrac{1}{2}|\Gamma|E^2 \cos(\theta_M + \theta_1 - \theta_1). \qquad (17)$$

Equations (16) and (17) show that the QSG phase ($\theta_1$) jitter and drift are canceled in mixers 30 and 32. The lowpass filtered PSD mixer output signals can be represented by a phaser diagram, in which the phase of the signals is given by, $$\theta_M = \text{TAN}^{-1}\, e_x/e_y, \qquad (18)$$

and the magnitude, $$\tfrac{1}{2}|\Gamma| = \sqrt{e_x^2 + e_y^2}. \qquad (19)$$

The magnitude of the bridge voltage ratio is, $$|\Gamma| = \frac{2\sqrt{e_x^2 + e_y^2}}{E^2}. \qquad (20)$$

The magnitude of the bridge voltage ratio is determined by the ADC 18 measurement of $e_x$ and $e_y$. The value of E is determined during calibration of system 10. The microcomputer 22 includes a program with routines to compute $\theta_M$, $\Gamma$, and Z.

With reference to QSG 20, the admittance of patch antennas 12 are measured throughout the frequency band ($BW_M$) of resonant frequencies associated with the range of ice and ice-water depths. The measurement band of frequencies may exceed 160 MHz. The frequency of QSG 20 is automatically swept up and/or down by control signals from microcomputer 22 until a resonant frequency for a particular patch antenna 12 is detected. At such resonant frequency, the imaginary part of the antenna input admittance (susceptance) exhibits a value of zero. Quadrature radio frequency signals are applied to the bridge 14 and PSD 26 networks. Microcomputer 22 computes the admittance from the measured values of $e_x$ and $e_y$.

The searches for the resonant frequencies of antennas 12 may initially start with the output frequency of QSD 20 at a lowest frequency in a predetermined measurement band. The admittances of antennas 12 are measured at this lowest frequency. The output frequency is then incrementally increased, and the respective admittance measured, until the antenna input susceptance demonstrates a minimum value. At least ten different points within the bandwidth of each microstrip antenna 12 are preferably used for each of the incremental output frequency changes. Since the three decibel (dB) bandwidth points of antenna 12 will be separated by approximately three percent of the resonant frequency, an increment frequency changes are preferably smaller than 0.003 of the operating frequency, e.g., 2.4 MHz or smaller increments at 800 MHz resonant frequency. Higher frequency resolution than this is not strictly required in system 10.

An in-phase ($e_I$) and a quadrature ($e_Q$) radio frequency signal are generated in QSD 20 network, which is essentially a frequency synthesizer with digital control originating in a frequency search program included in microcomputer 22.

Figure 5:
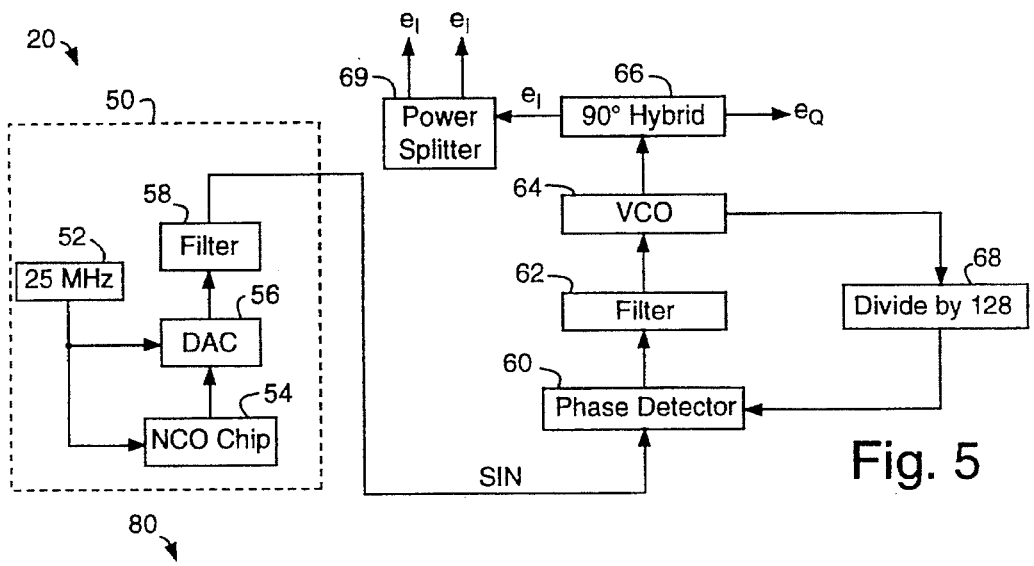
FIG. 5 is a block diagram of the quadrature signal generator included in the system of FIGS. 1 and 4.

QSG 20 is illustrated in further detail in FIG. 5. A numerically controlled oscillator (NCO) 50 includes a twenty-five MHz oscillator 52, an integrated circuit (IC) device 54, an eight-bit digital-to-analog converter (DAC) 56 and an anti-aliasing filter 58. NCO 50 produces a signal output (SIN) that is applied to one input of a phase detector 60. A filter 62 passes the output of phase detector 60 to control a voltage-controlled oscillator (VCO) 64. A 90° hybrid 66 generates the two quadrature signals, $e_I$ and $e_Q$, which are preferably synthesized within a common measurement band. A divide-by-128 counter 68 returns a sample of the output of VCO 64 for phase-locking. A power splitter 69 provides two copies of signal $e_I$. VCO 64 operates in a measurement band that extends from 600 MHz to 1200 MHz. VCO 64 may comprise a Vari-L VCO-120 integrated circuit, which is commercially available. The VCO output signal may alternatively be applied to a power splitter which provides radio frequency input signals to 90° hybrid 66 and the divide-by-128 counter 68. The 90° hybrid 66 generates the quadrature radio frequency signals required in the direct conversion process, and may be comprised of an Adams-Russel 90° hybrid model JH-140 which provides quadrature signals within a band of 500 MHz to 1000 MHz, and with an insertion loss of less than 0.3 dB. The quadrature deviation of such a unit is less than two degrees across the frequency band.

In operation, phase detector 60 and filter 62 force the frequency and phase of the NCO signal (SIN) and the VCO divide-by-128 signal to be identical. The divide-by-128 signal frequency typically extends from 4.6875 MHz to 9.3750 MHz. If the upper tuning band frequency is restricted to 1000 MHz by 90° hybrid 66, then the upper divide-by-128 signal frequency limit will be approximately 7.8125 MHz.

Device 54 is preferably a Stanford Telecom numerically-controlled oscillator product number STEL-1179, which is a CMOS device provided in a 26-pin plastic leaded chip carrier (PLCC) and that can be tuned with a 24-bit serial interface with microcomputer 22. Device 54 provides the granularity of digital tunability required in the frequency synthesis process. With a twenty-five MHz clock, the incremental frequency tuning step is 1.5 Hz. The incremental tuning ability of the frequency synthesizer as a whole is 192 Hz (128×1.5). A Vectron C0-442 CMOS clock oscillator may be used for oscillator 52. Anti-aliasing filter 58 can be realized with a Mini Circuits low pass filter.

The $e_I$ and $e_Q$ radio frequency signals may be applied to bridge 14 and PSD 26 in either a direct-conversion frequency transposition processes, as illustrated in FIG. 4, or dual-conversion frequency transposition processes. The direct conversion design has the advantage of circuit simplicity.

Figure 6:
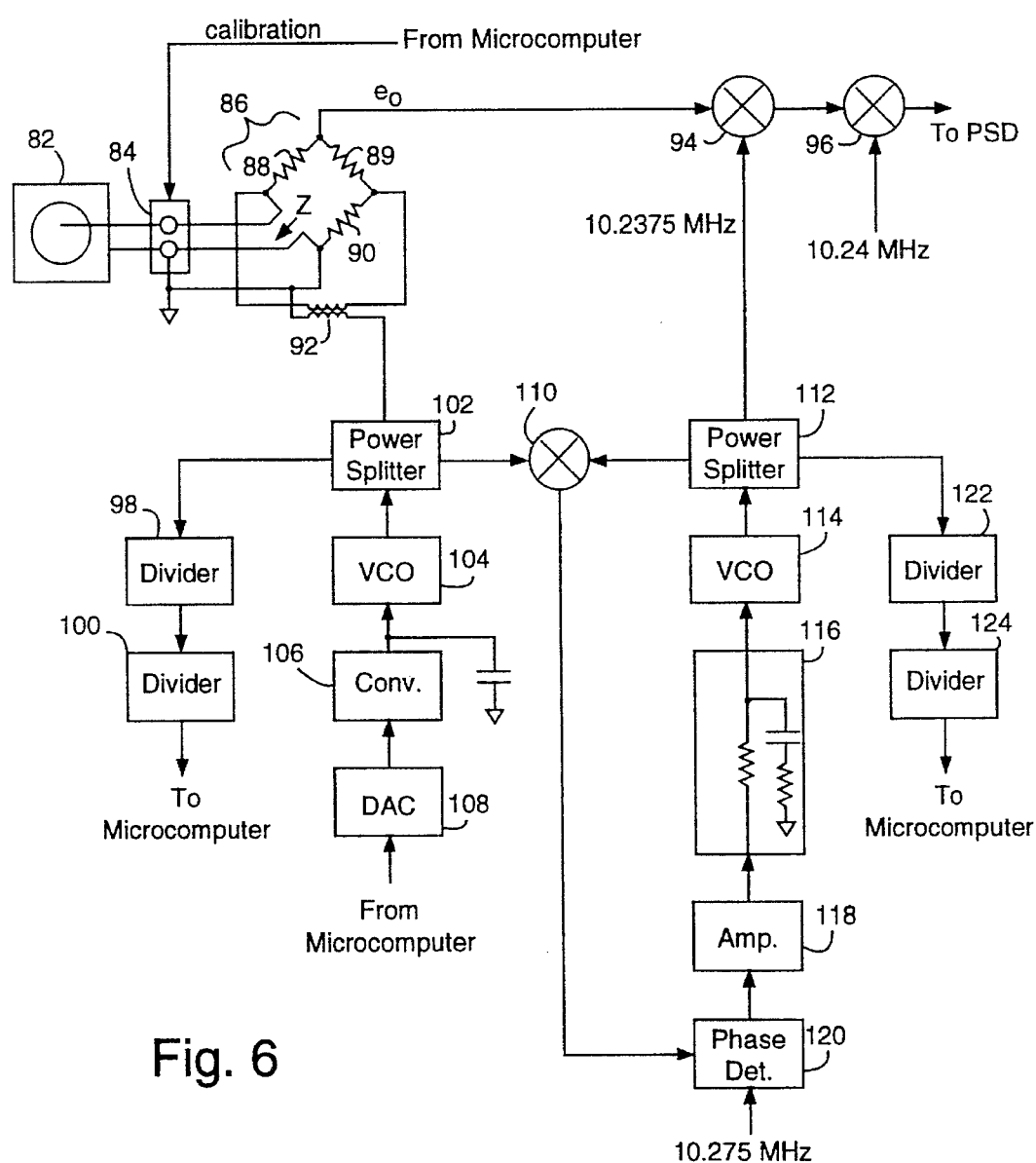
FIG. 6 is a combination schematic and block diagram of a portion of a dual-conversion embodiment of the present invention, and is otherwise similar to that of FIGS. 1 and 4.

An exemplary dual-conversion scheme is illustrated in FIG. 6. A second instrument embodiment of the present invention, referred to herein by the general reference numeral 80, comprises an antenna 82, an antenna switch 84, a bridge 86 including a set of three resistors 88–90 and a transformer 92, a first IF mixer 94, a second IF mixer 96, a first divider 98, a second divider 100, a first power splitter 102, a first VCO 104, a voltage converter 106, a DAC 108, a PLL mixer 110, a second power splitter 112, a second VCO 114, a filter 116, an amplifier 118, a phase detector 120, a third divider 122 and a fourth divider 124. Mixer 94 accepts a local oscillator (LO) frequency of 10.2375 MHz and mixer 96 uses a LO frequency of 10.24 MHz. An IF frequency of 2.5 KHz is the result and is forwarded to the phase sensitive detector.

In the context of FIG. 1, such a dual-conversion scheme necessitates that another intermediate frequency (IF) stage be positioned between the output port of the bridge and the phase sensitive detector. The dual-conversion scheme is such that the $e_I$ and $e_Q$ signals are generated at only the second IF frequency. The radio frequency signal applied to bridge 14 and first IF mixer are synthesized in the measurement frequency band to produce a constant first IF signal frequency.

The direct and dual-conversion schemes thus employ mixers, filters, and other radio signal processing components to achieve up-frequency conversion. Mixers serve to transpose frequency bands, while doublers and phase locked loops can be used to multiply the frequency (phase) of lower-frequency signals. All the radio frequency signals originate from a common crystal controlled clock so that a phase coherent frequency transposition process can be realized. Frequency tunability comprises digital programming of the frequency of signals.

Alternative configurations of the direct conversion scheme may use frequency doublers and mixers to synthesize the measurement band signals. Up-converter circuits using large integer multiplication of the NCO output signal yield conversion losses of more than eighteen dB. Although the frequency resolution would be degraded by the multiplication factor involved, the resolution would nevertheless be within the frequency step tuning requirements of system 10. Mixing of the NCO output signal with 600 MHz crystal oscillator may also be considered, which thereby reduces the multiplication factor. A doubler following the mixer may be used to achieve the appropriate band frequencies. Such circuit schemes require narrow bandpass filters to suppress unwanted frequency components. Mixer frequency transposition further requires suppression of the image band mixer injection signals. Unwanted signal rejection requirements can be relaxed when an NCO output signal is multiplied prior to mixing. Bandpass filtering of the NCO alias band might also be used. However, the amplitude would change in the NCO synthesized output signal band. Up-conversion schemes using only low pass filters require multiple mixers in the frequency transposition process.

In the dual-conversion process illustrated in FIG. 6, VCO 104 is controlled by a DC tuning voltage generated by DAC 108. A digital tuning code is generated by a microcomputer 22 and serially communicated to DAC 108. VCO 104 is part of a mix-down type PLL. The PLL produces an output frequency that is always 10.2375 MHz away from the measurement frequency of VCO 104. A first IF signal frequency is always 10.2375 MHz. The first IF signal is within a gain constant of the output signal of bridge 86. The first IF output signal is mixed with a 10.24 MHz signal in the second mixer 96. A second IF signal at 2500 Hz is applied to the phase sensitive detector. The 10.2375 and 10.24 MHz signals are generated by a coherent frequency source (CFS) circuit, which also generates quadrature signals for the PSD mixers, e.g., mixers 30 and 32.

Microcomputer 22 (FIG. 1) includes a program that computes the admittance of the antenna, generates incremental tuning signals for QSD 20, and performs a modulation function for transmitting data to a remote receiver. The microcomputer 22 may comprise a Dallas Semiconductor DS-5000T that has been programmed with the algorithms needed in measuring instruments 10 or 80. The DS-5000T includes 32K bits of non-volatile RAM. The standard Intel 80C51-type instruction set is used in programming the unit. Microcomputer 22 can preferably be powered down between instrument measurement periods to save power and prevent heating. It takes approximately twenty milliseconds to make an ice thickness measurement from an off-condition. System 10 can therefore operate on a low duty cycle, since ice layer thicknesses do not change very rapidly in the typical application.

The measurement of antenna admittance requires a four-quadrant inverse tangent program which determines the phase of the output voltage ratio ($\Gamma$) of bridges 14 or 86. The magnitude (E) of the bridge signal is determined in a second calibration program. This data is used in a third program to compute the admittance of the antenna. If the susceptance is not sufficiently small, microcomputer 22 generates an incremental tuning signal for the frequency generator to find a frequency point of reduced antenna susceptance.

Once the resonant frequency and conductance have been determined, a frequency modulator program within microcomputer 22 causes the signal applied to the antenna to be frequency modulated with digital modulation. The operational role of the antenna is thus changed from that of a sensor to a more traditional role of a radio transmitter antenna. The modulation conveys the resonant frequency, conductance, ice thickness, surface temperature and station source identification numbers of the particular instrument. A "dithered" frequency transmission may be used to permit multiple units to be operated such that one remote receiver can receive over time all the transmitted signals without excessive interference between simultaneously transmitting instruments.

A sleep timer program within microcomputer 22 may be included to reduce the power consumption duty cycle of the whole of systems 10 and/or 80. The benefit of this reduced power duty cycle can be illustrated by example. If measurements are made every minute, the resulting duty cycle can be as little as 0.0003. Estimated demand current of system 10, for example, is approximately 500 mA. The sleep mode current is one hundred microamperes. Therefore, the average current will be only slightly more than one hundred microamperes. It is possible, therefore, to use batteries to power instruments 10 and 80 that can be expected to last years. To further extend battery life, a surface temperature sensor may be included that controls when the transmitter is activated. For example, when temperatures approach freezing. A self-contained, unattended instrument installation is thus practical.

Although the present invention has been described in terms of the presently preferred embodiments, it is to be understood that the disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. An aircraft ice detection system, comprising:

an array of antennas having a flat shape for conformably mounting to a surface of an airfoil of said aircraft each antenna having a resonant frequency and an input admittance affected by ice when formed proximate to said antenna;

a calibration antenna having a flat shape for conformably mounting to said airfoil surface and having means for providing a standard reading of a simulated ice condition;

antenna selection means connected to each antenna in the array of antennas and the calibration antenna for selecting amongst them;

resonant frequency and admittance value measurement means connected to the antenna selection means; and computer means connected to the resonant frequency and admittance value measurement means and having an output for indicating to a user the presence of ice and icing conditions on said airfoil surface.

2. The system of claim 1, wherein:

the resonant frequency and admittance value measurement means includes a Maxwell bridge connected to the antenna selection means and a phase detector connected to an output of said Maxwell bridge; and the computer means includes an analog-to-digital converter (ADC) connected between said phase detector and an included microcomputer, and a control program included in said microcomputer is provided for computing admittance of the antennas, using a pair of measured values for signals $e_x$ and $e_y$ that are acquired via said ADC.

3. The system of claim 1, further comprising:

a temperature sensor for mounting to said airfoil surface and connected to the computer means.

4. The system of claim 1, further comprising:

an acoustical sensor comprising a piezoelectric device for mounting on said airfoil surface and connected to the resonant frequency and admittance value measurement means through the antenna selection means for measurement of ice accumulations that affect the stiffness and therefore the resonant frequency of the acoustic sensor and provide additional data to the computer means for assessment of a formation accumulated on said airfoil surface.

5. The system of claim 3, wherein:

the computer means includes temperature reading means connected to the temperature sensor and program means for determining whether the temperature of said airfoil is progressing away from or toward an icing condition.

6. The system of claim 5, wherein:

the computer means further includes material discrimination means for deriving an interpretation of the material composition of substances in contact with one or more of said antennas and for combining this information with a temperature reading from the temperature sensor for predicting both a freezing temperature point and an estimated time before freezing.

7. An aircraft ice detection system, comprising:

an array of antennas having a flat shape for conformably mounting to a surface of an airfoil of said aircraft each antenna having a resonant frequency and an input admittance affected by ice when formed proximate to said antenna;

a calibration antenna having a flat shape for conformably mounting to said airfoil surface and having means for providing a standard reading of a simulated ice condition;

antenna selection means connected to each antenna in the array of antennas and the calibration antenna for selecting amongst them;

resonant frequency and admittance value measurement means connected to the antenna selection means and including a Maxwell bridge connected to the antenna selection means and a phase detector connected to an output of said Maxwell bridge;

a temperature sensor for mounting to said airfoil surface and connected to the computer means; and computer means connected to the resonant frequency and admittance value measurement means and including an analog-to-digital converter (ADC) connected between said phase detector and an included microcomputer, and a control program included in said microcomputer is provided for computing admittance of the antennas, using a pair of measured values for signals $e_x$ and $e_y$ that are acquired via said ADC, and further including temperature reading means connected to the temperature sensor and program means for determining whether the temperature of said airfoil is progressing away from or toward an icing condition, the computer means further including material discrimination means for deriving an interpretation of the material composition of substances in contact with one or more of said antennas and for combining this information with a temperature reading from the temperature sensor to predict both a freezing temperature point and an estimated time before freezing.

8. A spacecraft ice detection system, comprising:

an array of antennas having a flat shape for conformably mounting to a surface of a fuel tank of said spacecraft with each antenna having a resonant frequency and an input admittance affected by ice when formed proximate to said antenna;

a calibration antenna having a flat shape for conformably mounting to said tank surface and having means for providing a standard reading of a simulated ice condition;

antenna selection means connected to each antenna in the array of antennas and the calibration antenna for selecting amongst them;

resonant frequency and admittance value measurement means connected to the antenna selection means;

a temperature sensor for mounting to said tank surface; and computer means connected to the resonant frequency and admittance value measurement means and temperature sensor.

9. The system of claim 8, wherein:

the resonant frequency and admittance value measurement means includes a Maxwell bridge connected to the antenna selection means and a phase detector connected to an output of said Maxwell bridge; and the computer means includes an analog-to-digital converter (ADC) connected between said phase detector and an included microcomputer, and a control program included in said microcomputer is provided for computing admittance of the antennas, using a pair of measured values for signals $e_x$ and $e_y$ that are acquired via said ADC.

10. The system of claim 8, further comprising:

an acoustical sensor comprising a piezoelectric device for mounting on said tank surface and connected to the resonant frequency and admittance value measurement means through the antenna selection means for measurement of ice accumulations that affect the stiffness and therefore the resonant frequency of the acoustic sensor and provide additional data to the computer means for assessment of a formation accumulated on said tank surface.

* * * * *